United States Patent
Perrona et al.

(12)

(10) Patent No.: US 6,478,968 B1
(45) Date of Patent: Nov. 12, 2002

(54) METHOD FOR FILTERING A THREE-PHASED REACTION MIXTURE

(75) Inventors: Philippe Perrona, Montluel (FR); Lionel Sever, Lyons (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/194,907

(22) PCT Filed: May 29, 1997

(86) PCT No.: PCT/FR97/00937

§ 371 (c)(1),
(2), (4) Date: Mar. 17, 1999

(87) PCT Pub. No.: WO97/46306

PCT Pub. Date: Dec. 11, 1997

(30) Foreign Application Priority Data

Jun. 4, 1996 (FR) .............................. 96 07169

(51) Int. Cl.[7] .............................. B01D 61/00
(52) U.S. Cl. ........................ 210/651; 210/650; 210/652; 558/459
(58) Field of Search ................. 210/651, 779, 210/196, 650, 652; 558/459

(56) References Cited

U.S. PATENT DOCUMENTS

| | | | |
|---|---|---|---|
| 2,166,183 A | | 7/1939 | Signaigo |
| 4,414,401 A | * | 11/1983 | Wintermeyer et al. |
| 4,511,454 A | * | 4/1985 | Bonny |
| 4,601,859 A | * | 7/1986 | Galle et al. |
| 4,756,821 A | * | 7/1988 | Giuliani et al. |
| 5,490,936 A | * | 2/1996 | Leupold et al. |

FOREIGN PATENT DOCUMENTS

| | | |
|---|---|---|
| DE | 32 45 318 | 6/1984 |
| EP | 0 052 719 | 6/1982 |
| EP | 0 235 003 | 9/1987 |
| EP | 0 599 180 | 6/1994 |
| WO | 91 16294 | 10/1991 |

OTHER PUBLICATIONS

Patent Abstracts of Japan, vol. 017, No. 388 (C–1086), Jul. 12, 1993 & JP 05 068869 (Asahi Chem Ind Co Ltd) Mar. 23, 1993, see abstract & Database WPI, Section Ch, Week 9317 Derwent Publications Ltd., London, GB; Class E19, AN 93–136921, see abstract.

Patent Abstracts of Japan, vol. 018, No. 134 (C–1176), Mar. 4, 1994 & JP 05 317867 A (Japan Orano Co Ltd), Dec. 3, 1993, see abstract & Database WPI Section Ch, Week 9402 Derwent Publications Ltd., London, GB, Class D15, AN 94–011316, see abstract.

* cited by examiner

*Primary Examiner*—Ana Fortuna
(74) *Attorney, Agent, or Firm*—Burns, Doane, Swecker & Mathis, L.L.P.

(57) ABSTRACT

A method for filtering a three phase reaction mixture comprising a liquid phase, an undissolved solid catalytic phase and a gas phase includes tangentially filtering through a membrane filter at least part of the three phased reaction mixture, and recycling the catalyst while recuperating at least part of the filtrate comprising the reaction products.

32 Claims, No Drawings

METHOD FOR FILTERING A THREE-PHASED REACTION MIXTURE

The present invention relates to a process for filtering a three-phase reaction mixture comprising a liquid phase, a non-dissolved solid catalytic phase and a gaseous phase.

In processes using a compound comprising at least one nitrile function and a non-dissolved catalyst of Raney nickel or cobalt type, it has been observed that in the absence of gas, and more particularly in the absence of hydrogen, the nitrile functions of the medium have a harmful influence on the activity of the catalyst.

Thus, in particular in the processes for the hydrogenation of nitriles into amines, and even more particularly in processes for the partial hydrogenation of a dinitrile into aminonitrile, the Applicant has demonstrated that the catalyst of Raney nickel or cobalt type has a tendency to become deactivated in the presence of nitrile functions, when the medium no longer or only sparingly contains hydrogen.

Moreover, it turns out that metal catalysts deposited on a support, which are also used, in particular in hydrogenation processes, separate out poorly by settling and are difficult to filter.

The present invention proposes a solution to these problems, which consists in tangentially filtering, on a membrane filter, at least some of a three-phase reaction mixture comprising a liquid phase in which nitrile functions are found, a gaseous phase comprising hydrogen and a catalytic solid phase comprising Raney nickel and/or cobalt or a supported metal catalyst, and in recycling the catalyst while at the same time recovering at least some of the filtrate containing the reaction products.

The tangential circulation, relative to the membrane and at high speed, of the mixture to be filtered minimizes the amount of solid retained on the filter. It is thus possible to minimize the risks of deactivation of the catalyst. It allows continuous filtration while at the same time keeping the catalyst in its reaction medium.

Generally, the circulation speed of the reaction mixture through the membrane is between 0.5 meter/second and 20 meters/second and preferably between 1 meter/second and 10 meters/second.

The membrane filters used for the tangential filtration generally consist of a flat or tubular support and an inorganic or organic membrane, often referred to as the active layer, which is a few micrometers in thickness.

For the process of the invention, the membranes used will preferably be inorganic membranes which generally behave better chemically and thermally with respect to the reaction mixture used.

The support and the active layer can be made of the same material or of different materials. The active layer of the filter can be made, for example, of α-alumina, zirconium oxide, titanium dioxide or graphite fibres. The support can also be made of alumina, graphite, zirconium oxide or titanium dioxide.

The membrane is also characterized by its mean pore diameter. Generally, this mean pore diameter ranges between 1 nanometer and one micrometer.

For reasons of lifetime and regenerability of the membrane, it is preferred in the present process to use ultrafiltration membranes which have a mean pore diameter of from 10 nanometer to 100 nanometer and a cutoff threshold (which is defined by the molecular mass of the compounds stopped by the membrane and is expressed in grams/mole or daltons) of greater than or equal to 5 kilodaltons (kD) and preferably greater than or equal to 100 kilodaltons.

The liquid phase of the reaction mixture to be filtered essentially comprises at least one compound containing nitrile functions, such as the unconverted starting dinitrile or nitrile, the aminonitrile and/or the amine and/or the diamine formed, and an optional solvent which can be, in particular, water and/or an amide and/or an alcohol and/or an amine and/or ammonia. The alcohols usually used are alkanols such as methanol, ethanol, 1-propanol, 2-propanol and 1-butanol, diols such as ethylene glycol and propylene glycol, polyols or mixtures of the said alcohols. When the solvent is an amide, use may be made in particular of dimethylformamide and dimethylacetamide. Among the amines which can be used as solvent, mention may be made, for example, of the amine, the diamine or the aminonitrile corresponding to the nitrile or the dinitrile which is hydrogenated. The liquid phase also generally comprises a strong inorganic base derived from an alkali metal or alkaline-earth metal.

When water is present with another solvent, the said solvent represents, on a weight basis, from two to four times the weight of water.

The solid catalytic phase generally consists of a catalyst based on Raney nickel and/or Raney cobalt, optionally, but preferably, comprising a doping element chosen from the elements from Groups IVb, VIb, VIIb and VIII of the Periodic Table of the Elements as published in the Handbook of Chemistry and Physics, 51st edition (1970–1971).

The catalyst based on Raney nickel and/or Raney cobalt used in the process can thus comprise, besides nickel or cobalt and the residual amounts of the metal eliminated from the original alloy during the preparation of the catalyst, i.e., generally, aluminium, one or more other doping elements, such as, for example, chromium, titanium, molybdenum, tungsten, iron or zinc.

Among these doping elements, chromium and/or iron and/or titanium are considered as the most advantageous. These doping elements usually represent, on a weight basis relative to the weight of nickel, from 0% to 15% and preferably from 0% to 10%.

The catalytic phase can also consist of a metal, which is generally a metal from Group VIII of the Periodic Table of the Elements, such as ruthenium, rhodium, nickel or cobalt, deposited on a support which is generally a metal oxide, such as aluminas, silicas, aluminosilicates, titanium dioxide, zirconium oxide or magnesium oxide.

In the supported metal catalysts, the metal generally represents from 0.1 to 80% of the weight of the support, and preferably from 0.5 to 50%.

The solid phase generally represents from 1% to 50% by weight relative to the weight of the liquid phase, without these values being critical.

The gaseous phase consists essentially of hydrogen.

The tangential filtration can be carried out at a temperature which is advantageously that at which the hydrogenation reaction is carried out. This temperature is usually less than or equal to 150° C., preferably less than or equal to 120° C. and even more preferably less than or equal to 100° C.

In concrete terms, this temperature is usually between room temperature (about 20° C.) and 100° C. The process can be performed, without any technical difficulties, at a temperature below 20° C., but there is no advantage in doing so on account of the lower production efficiency of the hydrogenation reaction.

The pressure difference between the filter inlet and outlet, which is required for the filtration, can be provided in part by the pressure at which the hydrogenation reaction is carried out. However, it is necessary to create a pressure greater than atmospheric pressure. Generally, this pressure is between 1 bar (0.10 MPa) and 20 bar (1 MPa) and preferably between 2 bar (0.5 MPa) and 10 bar (5 MPa). In practice, the pressure is created by a pump which feeds the membrane filter from the reactor.

The flow feeding the membrane filter obviously depends on the amount of reaction mixture present in the reactor, as well as the capacity of the filter. It is also determined according to the reaction progress, such that the liquid filtrate or permeate, which will be at least partially recovered and treated elsewhere, contains sufficient amounts of the intended product(s) of the hydrogenation reaction.

The catalyst filtered in the presence of hydrogen remains active and is recycled into the hydrogenation reaction.

The example which follows illustrates the invention.

EXAMPLE

A reactor fitted with a stirrer, means for heating and cooling, means for introducing reagents at its top part and removal means at its bottom part, contains about 20 liters of a mixture composed, on a weight basis, of:

20.1% adiponitrile 51.4% aminocapronitrile 9.1% hexamethylenediamine 14.2% water 5.2% Raney nickel with a mean particle size of about 10 micrometers.

This solution is at a hydrogen pressure of 2 bar and at a temperature of 55° C.

A volumetric pump with a flow rate of 2 m$^3$/h is placed at the removal outlet located at the bottom of the reactor, followed by an electromagnetic flow meter and a manometer. The solution removed from the reactor feeds a membrane filter consisting of a graphite support and an inorganic active layer of zirconium oxide with a cutoff threshold of 300 kD and a mean pore diameter of between 25 and 50 nm (trade name Carbosep M9 from the company Tech-Sep).

The filter-feed flow is placed under a hydrogen pressure of 2 bar and the circulation speed of the reaction mixture through the membrane is about 5 m/s.

The flow of permeate is 67 kg/h.m$^2$. The permeate is at atmospheric pressure.

No Raney nickel is found in the permeate.

The retentate containing the catalyst is recycled into the reactor.

Under these conditions, the concentration of catalyst in the retentate is constant and also at its initial value.

What is claimed is:

1. A process for hydrogenation of nitrile compounds to produce reaction products, the process comprising the steps of:
   (i) providing a three phase reaction mixture comprising a liquid phase containing nitrile functions, a gaseous phase comprising hydrogen, and a solid catalytic phase comprising at least one of Raney nickel, Raney cobalt, and a supported metal;
   (ii) subjecting the reaction mixture to tangential filtration, including passing the reaction mixture through a membrane filter, to render a retentate comprising the catalytic phase and a permeate comprising the reaction products; and
   (iii) recovering at least some of the permeate and recycling the catalytic phase back into the reaction mixture.

2. The process according to claim 1, wherein the membrane filter used for the tangential filtration comprises of a flat or tubular support and of an inorganic or organic membrane which is a few micrometers in thickness.

3. The process according to claim 2, wherein the membrane of the filter comprises α-alumina, zirconium oxide, titanium dioxide or graphite fibres and the support comprises graphite, alumina, zirconium oxide or titanium dioxide.

4. The process according to claim 2, wherein the membrane has a mean pore diameter ranging between 1 nanometer and one micrometer.

5. The process according to claim 4, wherein the membrane has a mean pore diameter of from 10 nanometer to 100 nanometers.

6. The process according to claim 1, wherein the at least one compound containing nitrile functions comprises at least one of an aminonitrile, an amine, or a diamine.

7. The process according to claim 6, wherein the compound containing nitrile functions comprises an unconverted starting dinitrile or nitrile, the aminonitrile and/or the amine and/or the diamine.

8. The process of claim 6, wherein the reaction mixture comprises a solvent.

9. The process according to claim 8, wherein the solvent comprises at least one of water, an amide, an alcohol, an amine, and ammonia.

10. The process according to claim 1, wherein the solid catalytic phase comprises a catalyst based on at least one of Raney nickel and Raney cobalt, optionally comprising a doping element chosen from the elements from Groups IVb, VIb, VIIb and VIII of the Periodic Table of the Elements as published in the Handbook of Chemistry and Physics, 51$^{st}$ edition (1970–1971).

11. The process according to claim 1, wherein the solid catalytic phase comprises a metal, which is a metal from Group VIII of the Periodic Table of the Elements deposited on a support which is a metal oxide.

12. The process according to claim 11, wherein the Group VIII metal comprises ruthenium, rhodium, nickel or cobalt.

13. The process according to claim 11, wherein the metal oxide is alumina, silica, aluminosilicate, titanium dioxide, zirconium oxide or magnesium oxide.

14. The process according to claim 1 wherein the tangential filtration is carried out at a temperature which is less than or equal to 150° C.

15. The process according to claim 14, wherein the temperature is less than or equal to 120° C.

16. The process according to claim 9, wherein the temperature is less than or equal to 100° C.

17. The process according to claim 1, wherein the pressure difference between the filter inlet and outlet is between 1 bar (0.10 MPa) and 20 bar (1 MPa).

18. The process according to claim 17, wherein the pressure difference is between 2 bar (0.5 MPa) and 10 bar (5 MPa).

19. The process of claim 1, wherein the nitrile compounds comprise dinitriles.

20. The process of claim 1, wherein the nitrile compounds are adiponitrile, and in the reaction mixture comprises aminocapronitrile and hexamethylene diamine.

21. The process of claim 1, wherein the gaseous phase consists essentially of hydrogen.

22. The process according to claim 1, wherein step (ii) further comprises passing the reaction mixture through the membrane filter at a circulation speed of 1 m/sec.–10 m/sec.

23. The process according to claim 1, wherein step (ii) further comprises providing a pressure difference between an inlet of the filter and an outlet of the filter of 2–10 bar.

24. The process according to claim 23, wherein step (ii) further comprises providing a pressure difference between an inlet of the filter and an outlet of the filter of 2–10 bar.

25. The process according to claim 1, wherein step (i) further comprises providing the reaction mixture within a reactor, and step (iii) further comprises recycling the retenate back into the reactor.

26. The process according to claim 25, wherein step (i) further comprises providing the reactor with a stirrer.

27. The process according to claim 26, wherein step (i) further comprises providing the reactor with a stirrer.

28. A process for hydrogenation of nitrile compounds to produce reaction products, the process comprising the steps of:
  (i) providing a three phase reaction mixture comprising a liquid phase containing nitrile functions, a gaseous phase comprising hydrogen, and a solid catalytic phase comprising at least one of Raney nickel, Raney cobalt, and a supported metal, in a reactor;
  (ii) subjecting the reaction mixture to tangential filtration, including passing the reaction mixture through a membrane filter, to render a retentate comprising the catalytic phase and a permeate comprising the reaction products; and
  (iii) recovering at least some of the permeate and recycling the retenate back into the reactor.

29. The process according to claim 28, wherein step (ii) further comprises passing the reaction mixture through the membrane filter at a circulation speed of 1 m/sec.–10 m/sec.

30. A process for hydrogenation of nitrile compounds to produce reaction products, the process comprising the steps of:
  (i) providing a three phase reaction mixture comprising a liquid phase containing nitrile functions, a gaseous phase comprising hydrogen, and a solid catalytic phase comprising at least one of Raney nickel, Raney cobalt, and a supported metal, in a reactor;
  (ii) subjecting the reaction mixture to tangential filtration, including providing a pressure difference between an inlet of the filter and an outlet of a membrane filter of 2–10 bar and passing the reaction mixture through the membrane filter, to render a retentate comprising the catalytic phase and a permeate comprising the reaction products; and
  (iii) recovering at least some of the permeate and recycling the retenate back into the reactor.

31. The process according to claim 30, wherein step (ii) further comprises passing the reaction mixture through the membrane filter at a circulation speed of 1 m/sec.–10 m/sec.

32. The process according to claim 31, wherein step (i) further comprises providing the reactor with a stirrer.

* * * * *